(12) United States Patent
Studer

(10) Patent No.: US 11,648,360 B2
(45) Date of Patent: *May 16, 2023

(54) GAS MIXTURE AND USE THEREOF FOR PEOPLE TO BREATHE AS REQUIRED IN THE EVENT OF PRESSURE DROPS IN AIRCRAFT OR IN THE EVENT OF HYPERVENTILATION, AND METHOD THEREFOR

(71) Applicant: CAELI NOVA AG, Pfaffikon (CH)

(72) Inventor: Marc Studer, Bachs (CH)

(73) Assignee: CAELI NOVA AG, Pfaffikon (CH)

( * ) Notice: Subject to any disclaimer, the term of this patent is extended or adjusted under 35 U.S.C. 154(b) by 36 days.

This patent is subject to a terminal disclaimer.

(21) Appl. No.: 15/539,242

(22) PCT Filed: Dec. 21, 2015

(86) PCT No.: PCT/EP2015/080770
§ 371 (c)(1),
(2) Date: Oct. 11, 2017

(87) PCT Pub. No.: WO2016/102450
PCT Pub. Date: Jun. 30, 2016

(65) Prior Publication Data
US 2018/0264213 A1     Sep. 20, 2018

(30) Foreign Application Priority Data

Dec. 24, 2014   (CH) ..................................... 02028/14

(51) Int. Cl.
*A61M 16/00*     (2006.01)
*A62B 7/14*      (2006.01)
(Continued)

(52) U.S. Cl.
CPC ......... *A61M 16/0045* (2013.01); *A61K 33/00* (2013.01); *A61M 16/10* (2013.01);
(Continued)

(58) Field of Classification Search
CPC ............ A62B 7/00–14; A62B 9/00–06; A62B 17/008; A62B 18/00–10; A62B 21/00;
(Continued)

(56) References Cited

U.S. PATENT DOCUMENTS 4,282,870 A     8/1981  Porlier
5,460,175 A    10/1995  Foote et al.
(Continued)

FOREIGN PATENT DOCUMENTS

CH          702 633 A1      8/2011
WO     2007/121773 A1     11/2007

OTHER PUBLICATIONS

International Search Report for PCT/EP2015/080770 dated Mar. 31, 2016.
(Continued)

*Primary Examiner* — Rachel T Sippel
(74) *Attorney, Agent, or Firm* — Sughrue Mion, PLLC

(57) ABSTRACT

Gas mixture used for ventilation of passengers and crew in emergency situations. Depending on the density altitude, it has 7±5% $CO_2$ at 15,000 ft flying altitude increasing to 17±5% $CO_2$ at 30,000 ft flying altitude. The carbon dioxide improves the bioavailability of oxygen in the body. The gas mixture is produced by additive dosage of $CO_2$ to either pure $O_2$ or to a gas mixture having a fraction of $N_2$ and a fraction of $O_2$. The method for ensuring good ventilation in case of loss of cabin pressure, or generally in case of hyperventilation, involves making the gas mixture above available via respiration masks. The use of such a gas mixture also for ensuring good ventilation of people with limited mobility, if (Continued)

Figure 1:
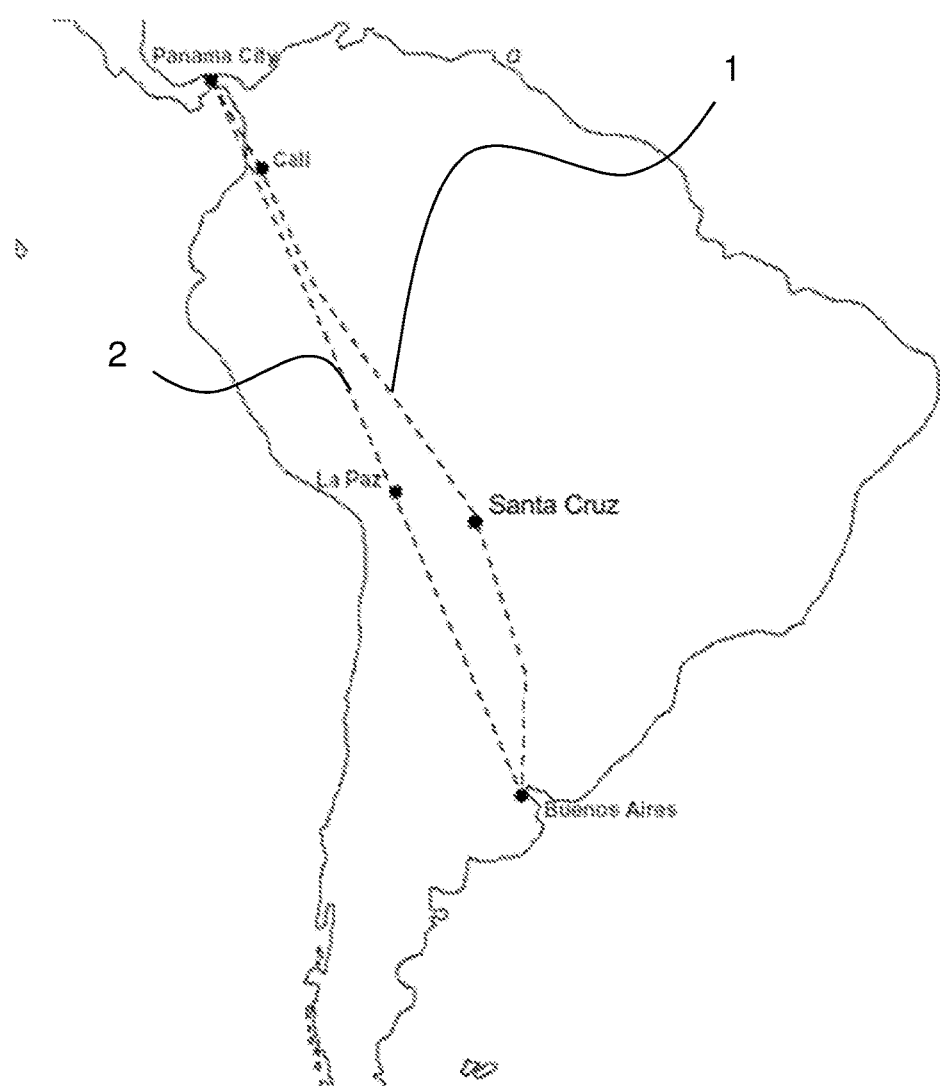

such ventilation is required. The prescribed amount of onboard oxygen for aircraft can thus be reduced and flight routes leading directly over high-altitude terrain may be taken.

6 Claims, 5 Drawing Sheets

(51) Int. Cl.
| | | |
|---|---|---|
| | *A61M 16/10* | (2006.01) |
| | *A62B 7/00* | (2006.01) |
| | *A61K 33/00* | (2006.01) |
| | *B64D 25/00* | (2006.01) |

(52) U.S. Cl.
CPC .................. *A62B 7/00* (2013.01); *A62B 7/14* (2013.01); *B64D 25/00* (2013.01); *A61M 2016/103* (2013.01); *A61M 2202/0225* (2013.01); *B64D 2231/025* (2013.01)

(58) Field of Classification Search
CPC .............. B64D 13/00–08; B64D 25/00; B64D 2205/00; B64D 2231/00–025
See application file for complete search history.

(56) References Cited

U.S. PATENT DOCUMENTS

| | | | |
|---|---|---|---|
| 5,647,345 A | | 7/1997 | Saul |
| 2009/0165796 A1* | | 7/2009 | Aubonnet ................. A62B 7/12 128/204.21 |
| 2009/0260631 A1* | | 10/2009 | Aubonnet ................. A62B 7/14 128/205.25 |

OTHER PUBLICATIONS

Stepanek et al., "Acute Hypoxic Hypoxia and Isocapnic Hypoxia Effects on Oculometric Features", Aviation, Space, and Environmental Medicine, vol. 85, No. 7, pp. 700-707, Jul. 2014.

Stepanek et al., "Early Detection of Hypoxia-Induced Cognitive Impairment Using the King-Devick Test", Aviation, Space, and Environmental Medicine, vol. 84, No. 10, pp. 1017-1022, Oct. 2013.

McFarland, "The Effects of Oxygen Deprivation (High Altitude) on the Human Organism", Technical Development Report No. 11, Civil Aeronautics Authority, United States Government Printing Office, 1941, pp. 1-79, Washington, DC (93 pages total).

"VII. Results of the Experiments with Excess Carbon Dioxide (3.0%) in the Low Oxygen and Low Pressure Chambers. Parts IV and V.", Effect of hypoxia on the human, 1938, pp. 61-66, 87-89 (22 pages total).

White, "Chapter 10 The Significance Of High Concentrations Of Carbon Dioxide In Aviation Medicine", Respiratory Physiology in Aviation, pp. 159-189 (1954).

"Effect of Changes in Blood $PCO_2$ on Brain Oxygenation at 147 MM. HG Ambient Pressure (39,000 Feet)", Technical Documentary Report No. SAM-TDR-62-70, School of Aerospace Medicine, Project No. 7756, Task No. 59692, Jun. 1962, p. 13 (2 pages total).

Dyer, "Chapter 18 Reading and other eye movements", Effects of Low and High Oxygen Tensions and Related Respiratory Conditions on Visual Performance: A Literature Review, Jun. 1988, pp. 199-203 (6 pages total).

Imray et al. "Effects of breathing air containing 3% carbon dioxide, 35% oxygen or a mixture of 3% carbon dioxide/35 % oxygen on cerebral and peripheral oxygenation at 150 m and 3459 m", Clinical Science, vol. 104, 2003, p. 203 (cover page only).

McFarland, "The Effects of Oxygen Deprivation (High Altitude) on the Human Organism", Civil Aeronautics Authority, Technical Development Report No. 11, May 1938, pp. I-VI, 1-79 (93 pages total).

\* cited by examiner

Track distance in nautical miles [NM]

Track distance in nautical miles [NM]

GAS MIXTURE AND USE THEREOF FOR PEOPLE TO BREATHE AS REQUIRED IN THE EVENT OF PRESSURE DROPS IN AIRCRAFT OR IN THE EVENT OF HYPERVENTILATION, AND METHOD THEREFOR

CROSS REFERENCE TO RELATED APPLICATIONS

This application is a National Stage of International Application No. PCT/EP2015/080770 filed Dec. 21, 2015, claiming priority based on Swiss Patent Application No. 02028/14 filed Dec. 24, 2014, the contents of all of which are incorporated herein by reference in their entirety.

The invention relates to a gas mixture as product and to the use of said gas mixture for artificial respiration of human beings as needed at high density altitudes. The invention further relates to a method for making the gas mixture available for artificial respiration. In particular, it relates to the use of a certain gas mixture as a product for artificial respiration in case of cabin depressurization in aircraft to ensure sufficient oxygen saturation of air passengers and crew, and to provide support in case of insufficient or lack of spontaneous breathing and hyperventilation, respectively.

A typical oxygen saturation is immanent in the human body, the value being dependent on age, clinical picture, and also on particular circumstances. The value indicates the fraction of oxygen-saturated haemoglobin in the blood, which provides information on the efficiency of breathing and oxygen transport in the body. Oxygen under-saturation in human beings arises either because the oxygen partial pressure in the environment is too low (corresponding to a height above 10,000 ft or 3048 m, for example) and/or as a consequence of health impairment. As there are different causes, the medical treatments vary equally. In general, a distinction is made between assisted ventilation and controlled (mandatory) ventilation. In the case of assisted ventilation, a ventilator machine has a purely support function to assist insufficient spontaneous breathing. The patient breaths himself and controls the breathing rate. By contrast, in case of controlled ventilation, the ventilator machine completely replaces the endogenous breathing function. The oxygen concentration of the artificially supplied air can be adjusted between a normal level concentration of 21% in the gas mixture, up to 100%, according to requirements. The inspired oxygen fraction is identified by $FiO_2$ (fraction of inspired oxygen). It is known that administering a $FiO_2$ higher than 0.5 (equivalent to an oxygen fraction of 50% in the respiratory air) for a prolonged period has harmful effects. Oxygen is a powerful oxidizing agent which also oxidizes other substances in the blood besides haemoglobin. However, enzymes in the body reverse this oxidation process. On the other hand, if pure oxygen is supplied to the body beyond a certain period of time, the "methaemoglobin reductase" cannot repair this damage given of the increased oxidation of haemoglobin and other proteins. When the endogenous anti-oxidation system is exhausted, the oxygen radicals released cause oxygen toxicity which is manifested in effects on the central nervous system, the lungs and vision. Nonetheless, patients in a life-threatening condition are ventilated—if only temporarily—with pure oxygen, i.e. with $FiO_2=1$. During pre-oxygenation as well, i.e. the prophylactic enrichment of the oxygen reservoir of the lungs—according to usual practice before anaesthetic induction for example—is performed by supplying 100% oxygen to the patient to flush the nitrogen of tidal air from the respiratory tract. In the same way, crew and passengers are ventilated with pure oxygen in the case of loss of cabin pressure in aircraft. Here, the prevailing argument is that a large quantity of oxygen should be introduced into body tissue as quickly as possible, as the occupants of the aircraft might already be suffering from an undersupply of oxygen. In this context, any adverse effects are therefore obviated or accepted.

However, the risks of ventilation are not attributable solely to the properties of oxygen. The concentration of carbon dioxide (CO2) in the (arterial) bloodstream also plays a critical role. Breathing control and regulation is primarily effected via chemoreceptors or chemosensors that are sensitive to the partial pressure of carbon dioxide (in this respect, oxygen-sensitive receptors and other receptors are less important). The level of carbon dioxide in the blood is thus a vegetative stimulus for breathing regulation. If the level of carbon dioxide in the blood exceeds a characteristic threshold value, respiratory stimulants are released. Conversely, in case of hyperventilation and the concomitant reduction of carbon dioxide partial pressure in the blood (hypocapnia), a reflex restriction is imposed on respiration. Thus, in order to suppress their breathing reflex, inexperienced divers often hyperventilate in order to exhale carbon dioxide and consequently remain under water for a longer time. However, this involves considerable risks, possibly resulting in a loss of consciousness and in the case of diving—drowning (known as shallow water blackout). As outlined in detail further below, symptoms of deficiency occur with decreasing endogenous carbon dioxide level, from unpleasant to life-threatening. Limited freedom of movement further amplifies the effect of hyperventilation, leading to a further decrease of the carbon dioxide level in blood. The reason for this is that the muscles then produce less endogenous carbon dioxide. Consequently, the symptoms of carbon dioxide deficiency occur more quickly and more severely. This problem is typical for the situation of loss of cabin pressure in aircraft, because passengers necessarily only have limited mobility. Thus, monitoring the carbon dioxide level in such a situation is imperative during ventilation, e.g. by measuring the end-expiratory partial pressure of carbon dioxide.

If the cabin pressure in an aircraft drops below a critical value, the ceiling compartments above the passengers' seats open and oxygen masks drop from their holders and are suspended in front of the passengers' faces. Pure oxygen flows into the masks through a supply tube and is then inhaled into the nose and mouth of the breathing person. The oxygen supplied to the passengers is either generated in chemical oxygen generators or carried in pressurized on-board gas cylinders, whereas the oxygen supplied to the pilots in the cockpit is released from a separate pressurized gas system. The amount of oxygen stored in an aircraft depends on the certification and intended use of the aircraft and also on the routes it is intended to fly. In this context, consideration must be given to whether the aircraft will fly mainly over land or sea, or whether it is designed to fly long distances over high-altitude terrain and mountainous areas.

The amount of time within which an individual remains able to perform flying duties efficiently while exposed to an environment of insufficient oxygen supply is referred to as time of useful consciousness (TUC) or Effective Performance Time (EPT). After this time, the body tissue and organs suffer from significant undersupply of oxygen and the body becomes hypoxic. Below a certain oxygen saturation of the brain, the ability to act rationally is lost, followed by loss of consciousness. The TUC is specified for a given flight level (the term flight level refers to a level of equal barometric pressure, corresponding to a given flying altitude expressed in hundreds of feet) and decreases with increasing flying altitude. The table below shows the average TUCs for various flight levels.

| Flight Level | TUC | Altitude in Meters | Altitude in Feet |
| --- | --- | --- | --- |
| FL 150 | ≥30 min | 4,572 | 15,000 |
| FL 180 | 20-30 min | 5,486 | 18,000 |
| FL 220 | 5-10 min | 6,705 | 22,000 |
| FL 250 | 3-6 min | 7,620 | 25,000 |
| FL 280 | 2.5-3 min | 8,534 | 28,000 |
| FL 300 | 1-3 min | 9,144 | 30,000 |
| FL 350 | 30-60 sec | 10,668 | 35,000 |
| FL 400 | 15-20 sec | 12,192 | 40,000 |
| FL 430 | 9-15 sec | 13,106 | 43,000 |
| ≥FL 500 | 6-9 sec | 15,240 | 50,000 |

The speed of decompression also affects the TUC: the more rapid the decompression, the shorter the TUC. This is why, given the rapidly occurring undersupply of oxygen to the body, rapid replacement of the oxygen supply is essential for survival, and military pilots who regularly fly at altitudes well above those of passenger air traffic wear their oxygen masks ready for use during the entire flight. There is no such necessity for civil aviation, because the cruising altitude of airliners is lower, namely between FL 250 and FL 450, which corresponds to a flying altitude of about 25,000 ft to 40,000 ft.

For commercial reasons, flight routes should ideally be optimized to the shortest route between two airports. Nowadays, the ranges of modern airliners allow direct (inter) continental flights to destinations which until a few years ago could only be reached with stopovers. However, for safety reasons not all direct routes are open to air traffic. Flying over high mountain ranges such as the Himalaya between India and Tibet, the Central Asian Hindu Kush and the South American Andes is only possible with restrictions and under certain conditions. The decisive requirements are dictated by two distinct emergency situations: engine failure on the one hand and loss of cabin pressure on the other. In the first case, the danger resides in the loss of thrust due to the failure of one or more engines, forcing it to reduce altitude, since an aircraft with reduced thrust cannot maintain its cruising altitude. In such cases, escape routes enable the aircraft to execute a drift-down to the closest possible runway. The ICAO (International Civil Aviation Organization), the EASA (European Aviation Safety Agency), the JAA (Joint Aviation Authorities) and as well the FAA (U.S. Federal Aviation Administration) all prescribe that such emergency escape routes must satisfy a standard according to which a vertical clearance of at least 2'000 ft from the ground must be assured during the engine-out drift-down manoeuvre to the OEI (one-engine inoperable) service ceiling. and when level flight is re-established a vertical clearance of 1'000 feet above the ground and 2'000 feet above mountains within a specific lateral distance relative to the flight path. The provisions of the regulatory authorities differ with regard to the specific lateral track width for said obstacle clearance.

If emergency landings were caused by engine failure only, the sophisticated system of escape routes would allow for almost any direct flight routes, notwithstanding some minor deviations. But the second case of a possible emergency situation, that is to say loss of cabin pressure, represents a substantially more restrictive set of problems. Besides the requirements mentioned above, the time factor is far more significant than in the case of engine failure. The number of potentially possible escape route is reduced considerably, because on many such routes the required difference in altitude cannot be attained within a sufficiently short time. The standard procedure in the event of loss of cabin pressure is regulated by the ICAO. It provides that—after safely breathing through their own oxygen masks—pilots initiate a descent as quickly as possible to bring the aircraft to a safer altitude, i.e. to a level at which humans can breathe without additional oxygen supply. This must be accomplished within the bridging time predefined by the oxygen supply. Due to limited space and weight capacity of an aircraft, the oxygen supply can be increased only at the cost of cargo or the maximum number of passengers. An improved ventilation of the passengers in case of cabin depressurization might thus also result in less oxygen having to be carried aboard the airplane, thus reducing the overall weight of the aircraft.

If the problem of artificial respiration did not exist, in many cases airliners would be able to fly to their destinations by a more direct route. If engine failure were the only limiting factor, multi-engine aircraft with passengers aboard would be able to overfly any region, because the escape route system allows for a drift-down to the one-engine inoperable service ceiling on any route section. In practice however, in order to qualify as emergency escape route, any such off-track route must meet the more restrictive set of requirements of the two above-mentioned emergency situations—i.e. that of spontaneous cabin depressurization. An improved ventilation system for passengers in the event of cabin pressure loss which would require less oxygen could extend the time interval imposed by a conventional oxygen supply. Consequently, it may not be necessary to implement safety precautions exceeding those prescribed for the case of engine failure. Without these additional limitations, itineraries could be flown over high-altitude terrain without detours and consequently thousands of tons of kerosene could be saved. The saving in fuel weight would enable either the loading capacity to be increased or the overall fuel consumption reduced, because the aircraft's weight is reduced by the deadweight of the reduced fuel requirement. This would also contribute to environmental conservation. Finally, flight times could be reduced considerably, offering not inconsiderable operational advantages as well as direct flights to more distant destinations.

The flight routes that are actively flown over extensive mountainous areas today involve substantial planning effort, besides actually carrying them out. In the event of major technical problems and malfunctions, it is primarily the pilots' responsibility to handle the emergency situation effectively, that is to take immediate decisions and implement the necessary steps. Since decisions in such situations are most often irreversible, the outcome of events is largely determined by humans who must react in these stress situations. Thus, a significant risk of errors with possibly fatal consequences is given a priori. A less urgent time factor or a longer decision period in emergency situations would increase the quality of decisions significantly and in doing so, contribute substantially to safety.

Therefore, it is the object of the present invention to provide a product and generally a method as well as a use of said product for the purpose of ventilation at high density altitudes or in case of hyperventilation, to ensure gas exchange with the human body and to improve body function and performance by providing more efficient artificial respiration in situations where such becomes necessary. The object of the present invention is further to provide a product, a method and use of said product which prolongs the period remaining between the instant when the oxygen is made accessible to the air passengers and the instant when the aircraft has descended to a safe flight altitude corresponding to a high-density altitude in which humans can survive, to such a degree that in case of cabin pressure loss, more time is available to the pilots to take measures and decisions respectively for minimizing danger and increasing general flight safety. It is a further object of the invention to provide a product, a method and the use of said product, so that a flight route need not necessarily comply with more restrictive itinerary-related requirements than in case of an engine failure scenario, such that an aircraft may descend more slowly in the event of a depressurization occurring. This is advantageous for itinerary-related reasons, as this allows more direct flight routes over high-altitude terrain. It is still another object of the invention to provide a product, a method and the use of said product, so that in the event of loss of cabin pressure the body functionality of the air passengers and crew is ensured using less oxygen than previous ventilation systems, thereby reducing or preventing harmful risks associated with the supply of pure oxygen. In particular, the invention is intended to help effectively avoid the occurrence of otherwise threatening symptoms for people in a situation such as prevails in an aircraft, i.e. in which physical movement is limited and susceptibility to complications from artificial respiration with pure oxygen is thus increased.

Regarding the first aspect, the problem is solved with a gas mixture for ensuring good ventilation of air passengers and crew in emergency situations, or generally in cases of hyperventilation, which is characterized in that depending on density altitude it comprises 7±5% $CO_2$ at 15,000 ft flying altitude, increasing to 17±5% $CO_2$ at 30,000 ft flying altitude, to act as bioenhancer and thus to improve the bioavailability of oxygen in the body, by additive dosage of the carbon dioxide to either pure $O_2$ or to a gas mixture comprising a fraction of $N_2$ and a fraction of $O_2$ for ventilation.

The object of the invention is also solved with a method for ensuring ventilation of people with limited mobility in emergency situations, or generally in cases of hyperventilation, in which the method is characterized in that artificial respiration masks are made available for placing over the nose and mouth, through which the gas mixture according to one of the claim 1 or 2 is continuously supplied upon fitting the mask to nose and mouth of the respective person.

Thirdly, the object of the invention is solved by the use of a gas mixture of one according to one of the claim 1 or 2 for ensuring good ventilation of people with limited mobility if needed, or generally in case of hyperventilation.

The product, the method and the use of said product are disclosed on the basis of the following explanations. The efficiency of the method has been demonstrated in many trials and measurements. The content thereof will be discussed in the following.

In the drawing

Figure 2:
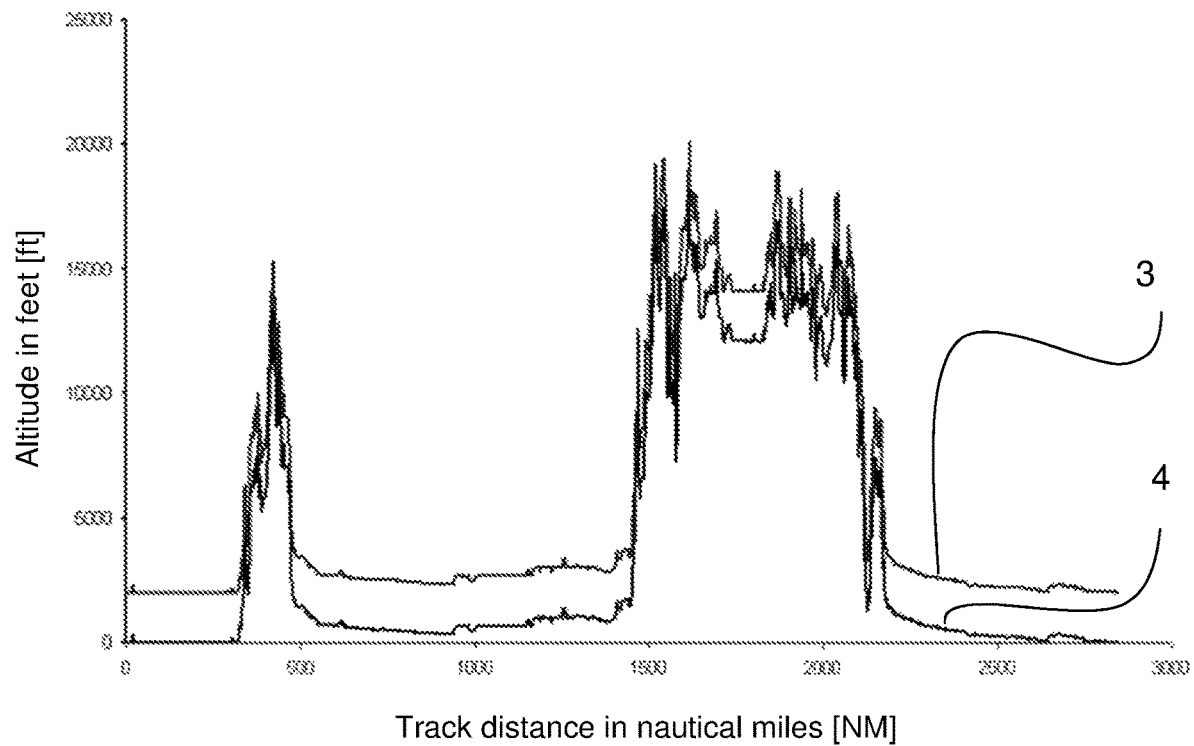
Figure 3:
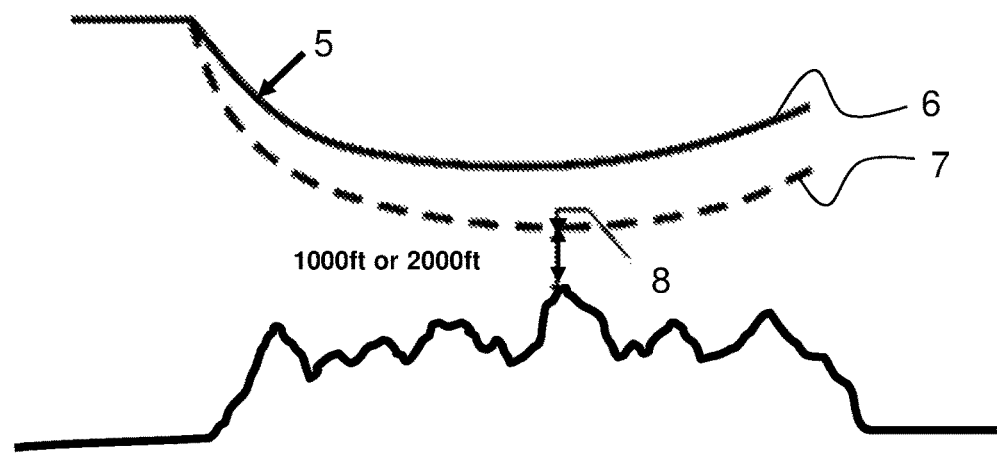
Figure 4:
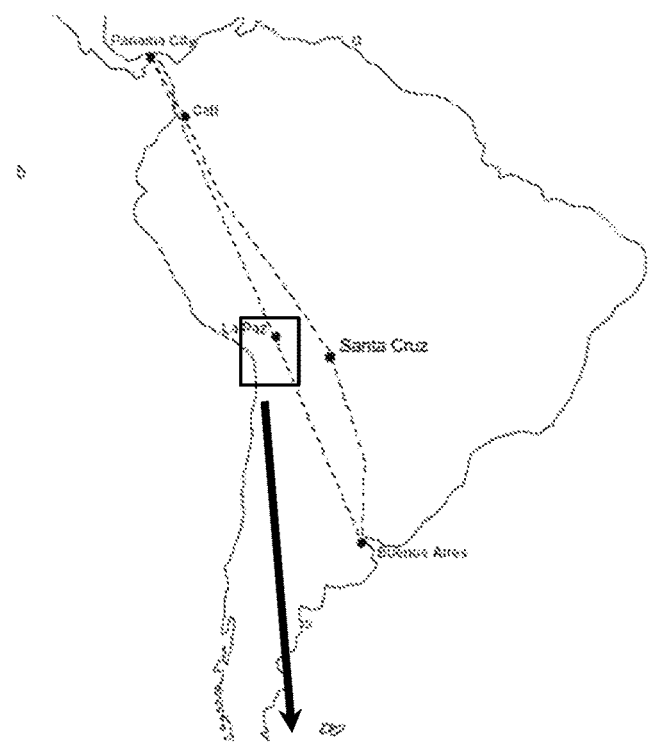
Figure 4:
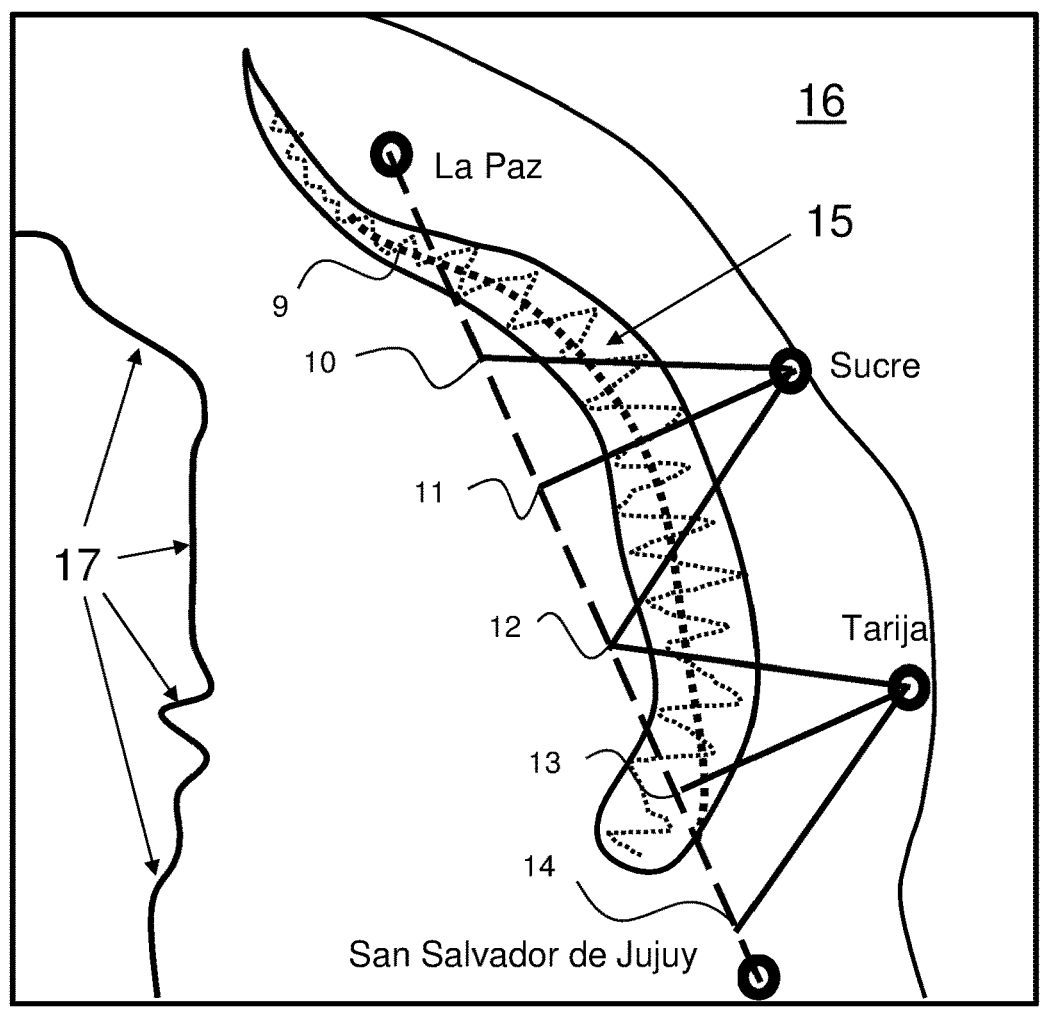
Figure 5:
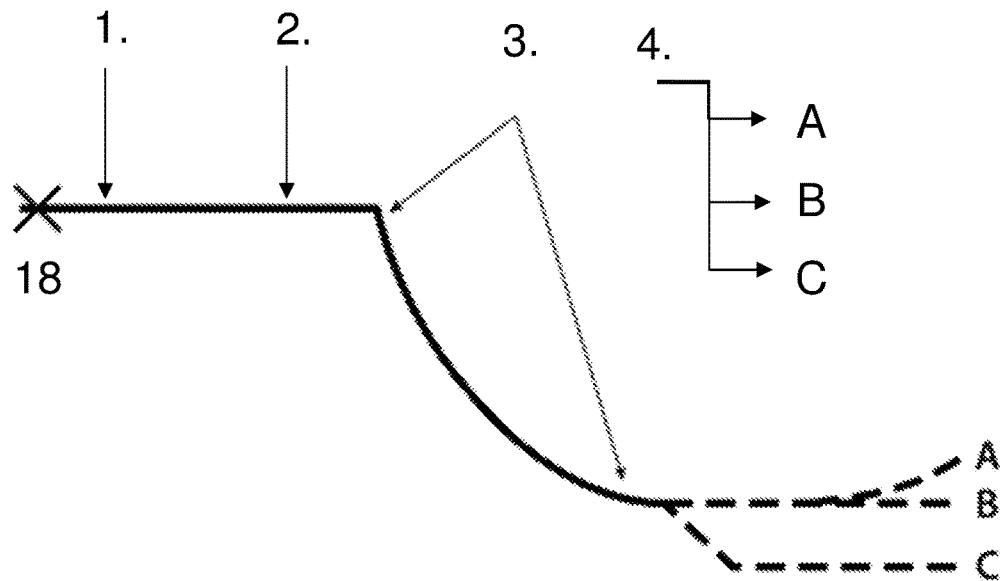
Figure 6:
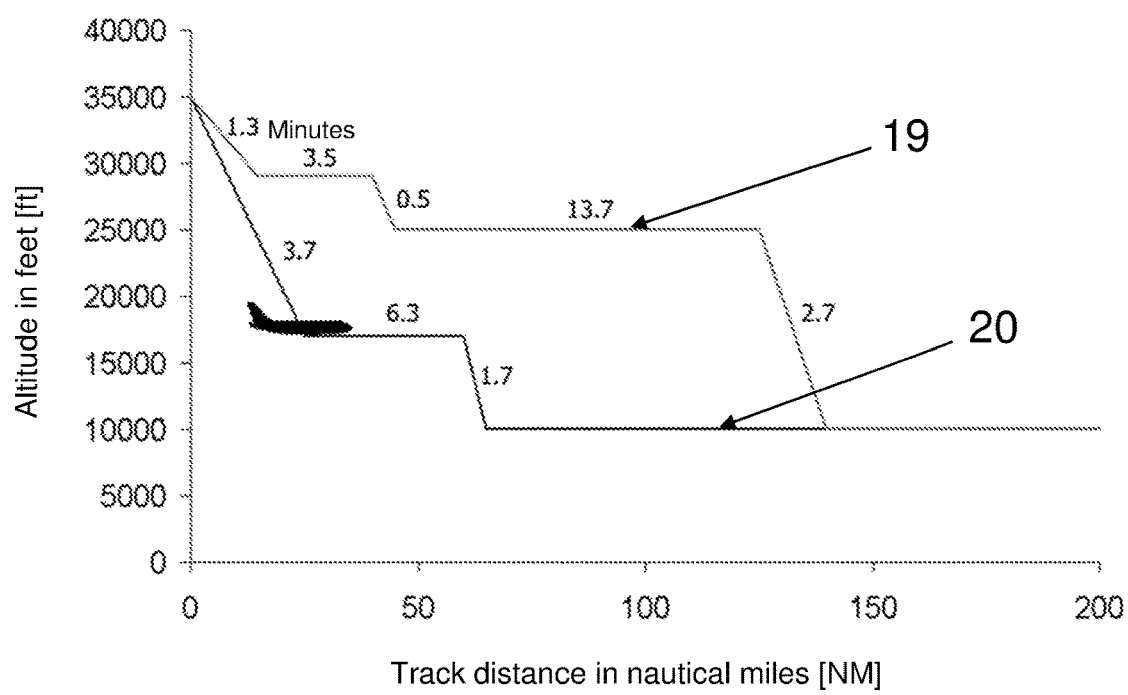
Figure 7:
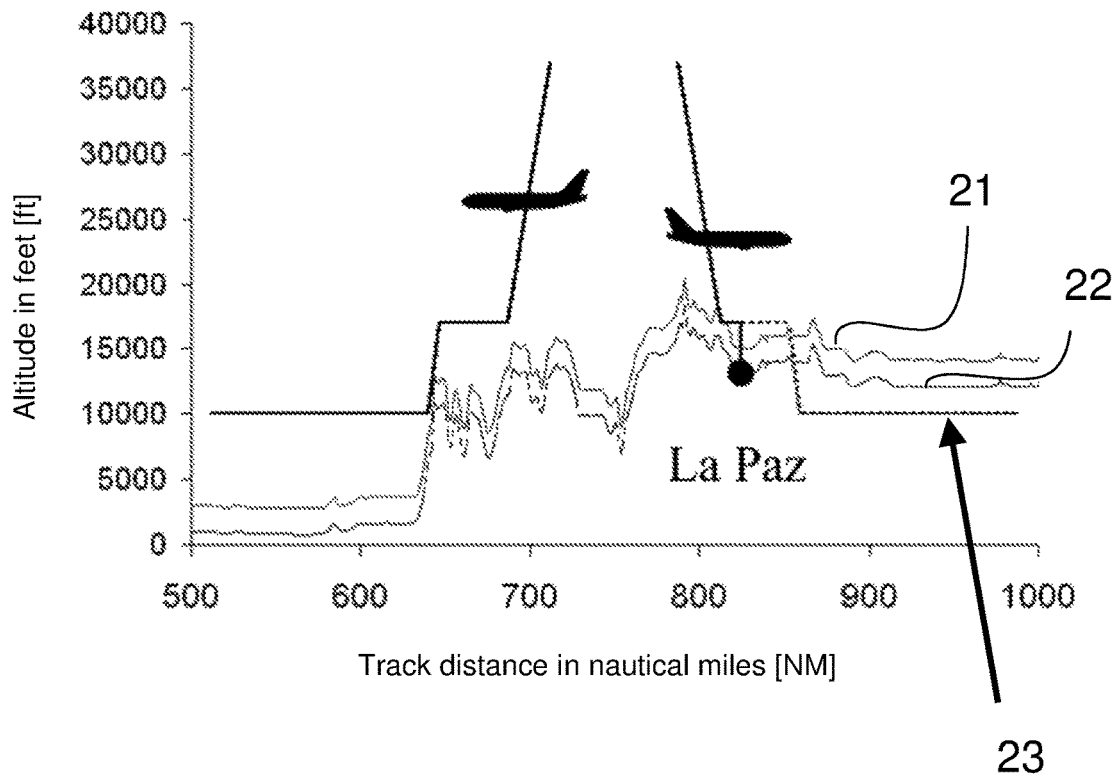
Figure 8:
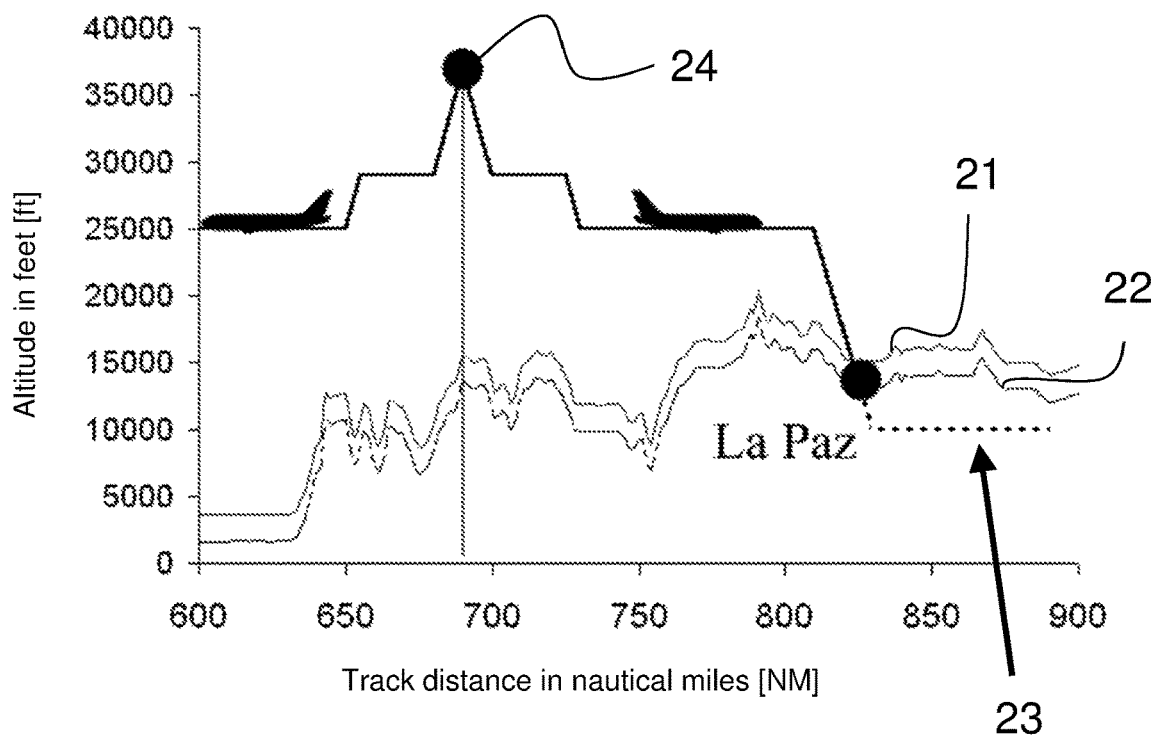

FIG. 1: shows a flight route modified due to the highly elevated terrain of the Bolivian-Argentinian Andean mountains;

FIG. 2: shows the associated altitude profile of the flight route with the required minimum ground clearance indicated by way of superposition on the altitude profile;

FIG. 3: shows a typical emergency descent profile of an aircraft to a reduced flight altitude;

FIG. 4: shows a flight route between La Paz and San Salvador de Jujuy with an exemplary system of escape routes;

FIG. 5: shows a procedure with options A, B, C for descent in an engine failure scenario;

FIG. 6: shows a 737-700 CFM56-7 emergency descent profile in the event of loss of cabin pressure for a standard descent in 15 minutes or optional descent in 22 minutes, respectively, provided by Boeing in accordance with the regulations set by ICAO;

FIG. 7: shows descent options according to a 12-minute descent profile for an aircraft in the high mountainous area around La Paz;

FIG. 8: shows descent options according to a 22-minute descent profile for an aircraft in the high mountainous area around La Paz.

FIG. 1 shows the implications of the constraints imposed on route planning due to the problem of ensuring adequate oxygen supply. This is illustrated by means of a flight route between Panama City and Buenos Aires. In the case of direct route, after about halfway the flight path passes over the Bolivian and subsequently the Argentinian Andes. Accordingly, this extensive and extremely high mountainous area constitutes a restriction on emergency descent options, because in the event of cabin depressurization over the extensive high plateau, the aircraft is unable to descend to a safe altitude where air passengers can breathe autonomously within the required time limit. For this reason, a substantially longer detour route 1 via Santa Cruz needs to be taken mostly over lowland, avoiding the critical Andes mountains. The economical and efficient variant of a direct route 2 therefore must not be used. The altitude profile associated with a direct route 2 between Panama City and Buenos Aires is represented in FIG. 2. The diagram shows two curves 3 and 4, wherein the lower curve 4 indicates the altitude profile corresponding to the geography of the terrain. Superimposed on this is the minimum vertical clearance 3 which an aircraft must observe at every point of the flight route. The prescribed descent profiles must therefore be higher than the mandatory ground clearance.

FIG. 3 illustrates a typical emergency descent profile of an aircraft following an engine failure. The actual trajectory 6 (net flight path) as well as the idealized trajectory 7 (gross flight path) as developed in flight route planning are indicated. In the event of engine failure during flight, a positive climb gradient must be attained after drift-down 5, when the airplane is at least 1,500 ft above the (emergency) landing site. The positive climb gradient is indicated in FIG. 3 at the lowest point 8 of the flight path (at least 2000 ft of vertical clearance above the ground or 1000 ft of vertical clearance in the level-off segment of lower flight routes). If a fully loaded aircraft cannot fulfil the required standards at every stage of its flight route, it is not permitted to fly that route.

An emergency escape route system complying with the regulatory safety provisions has been developed for all flight routes over high altitude mountains. An example of such a system is shown in FIG. 4, which represents the flight route over the Andes mountains between La Paz and San Salvador de Jujuy. The filled area 15 marked with a dotted zigzag line indicates very high terrain, and the area 16 to the right of the solid line indicates very low terrain, while the remaining white areas indicate moderate height. The territorial strip 15 along the flight route depicts the particularly high elevation of the Andes massif between Bolivia and Argentina. Route planning is determined primarily by the limited amount of oxygen aboard the airplane for supply to crew and passengers mentioned in the introduction. A route along this massif, which would thus constantly be over the high altitude terrain would therefore not be permitted. This is shown in FIG. 4 by the bold dotted line 9. The dashed, direct route from La Paz to San Salvador de Jujuy for example can be flown instead. In practice, local and aviation-related factors such as wind, temperature, local pressure, weight etc. can also lead to minor deviations from a potential route and therefore need to be determined specifically. It should be noted here that aircraft which fly such a specific route as indicated by this dashed straight are equipped with corresponding high-capacity gaseous emergency oxygen systems, as is explained in the following section. On the direct route between La Paz and San Salvador de Jujuy two ideal turn points 11 and 13 are shown, leading straight to the airports of Sucre or Tarija. The possible emergency escape routes are either perpendicular to the direct route (shortest emergency escape routes) or they represent two sides of an equilateral triangle (longest emergency escape routes). This creates a triangular escape area useful for orientation, enabling identification of the points marking the quickest possible descent (ideal turn points). The critical points 10, 12 and 14 that allow one or the other landing option to be considered are positioned exactly halfway between the "ideal turn points". The decision regarding the route effectively selected for an emergency descent is made by the flight captain.

Some airliners and business jets are equipped with high-capacity gaseous emergency oxygen systems, also known as burning systems (due to the heat generation resulting from the chemical reaction, by means of which oxygen can be produced aboard). Accordingly, a small number of airliners that cover long distances over high mountain regions are equipped with such high-capacity oxygen devices. However, the oxygen tanks and the essential equipment involved result in additional weight, which is detrimental to flight performance especially in the event of an engine failure, when only a reduced number of engines provide thrust. In such a scenario, the effective resulting OEI (one-engine inoperable) service ceiling depends on a series of factors, including the number of engines remaining operative, and particularly on the weight of the aircraft. The flight team needs to strictly adapt the procedure of an emergency drift-down to these conditions. FIG. 5 indicates the possible options. In each case, upon occurrence of an engine failure at point 18, as the first 1st measure the maximum continuous thrust is set immediately, as the 2nd measure airspeed is reduced, and as a 3rd measure drift-down is initiated at a defined drift-down speed. Depending on the situation, as a 4th measure a decision is then made regarding whether to adopt one of three options A, B or C, According to option A, airspeed is maintained after the drift-down and the aircraft climbs constantly to a higher flight altitude with continued fuel consumption (A). According to option B, the flight altitude is maintained for the remainder of the flight and airspeed is gradually increased to engine out long-range cruise speed, or according to option C altitude is reduced airspeed is increased immediately to engine-out long-range cruise speed. If after a drift-down, the required height of the flight path, i.e. at least the altitude required by option C, cannot be attained further along the airway due to high-altitude terrain, the aircraft's payload must be reduced, for example, by partially emptying or burn off of fuel, which allows a higher flight altitude (option A). However, this requires that an emergency landing site is available within a foreseeable distance. The aircraft weight is always a negative factor in an engine failure scenario. There is an inherent conflict between solving artificial respiration problems in the event of cabin depressurization on the one hand, and the required drift-down profiles in case of engine failure on the other. If the need for an efficient oxygen supply of air for passengers and crew takes precedence due to the altitude profile of the terrain covered by a certain flight route, the weight disadvantage of a more efficient oxygen supply system is considered. The additional time per meter of altitude thus gained in the event of cabin pressure loss allows longer escape routes, by which multiple off-track escape areas may be accessed. On the other hand, if the weight disadvantage cannot be compensated any longer, the route must not be flown. This is usually the case with routes covering extended high mountain areas.

In an event of cabin depressurization the specific provisions of ICAO apply. The specific descent profiles prescribed by different aircraft manufacturers or airlines, respectively are derived therefrom. In general, the ICAO prescribes two different drift-down profiles, a standard descent profile and an optional descent profile for exceptional routes. Two such profiles with specific values determined by Boeing are shown in FIG. 6, namely a 12-minute standard profile 20 and an optional 22-minute profile 19. The magnitudes of these values are the same for all aircraft manufacturers and airlines. Following cabin depressurization, an aircraft of the manufacturer Boeing (The Boeing Company) must have descended to 14,000 ft in 12 minutes or 22 minutes respectively depending on its certification. The intermediate altitudes and intermediate times specified in the respective profiles 19, 20 also have to be observed. A flight route must be selected such that an aircraft can adhere to these altitudes and times throughout the flight. Thus, when flying over extensive high mountain ranges, detours are necessary to be able to adopt with the prescribed descent profile and thus descend to a lower altitude quickly enough at all times if a loss of cabin pressure occurs. More direct flight routes over extensive high mountain areas can almost only be flown by cargo aircraft, because these carry a greater oxygen supply for the crew than airliners. As described previously, the planned flight path must also allow for the regulated procedures in case of an engine failure, as previously described. In this case, the descent profile 7 of FIG. 3 is decisive. Modern airliners are able to fly at considerably higher altitudes after an engine failure than those specified by the profiles in case of cabin depressurization. As a consequence, the limitations imposed on potential flight routes are primarily determined by a potential cabin pressure loss, specified by the emergency descent profiles 19, 20 according to FIG. 6. In general, all emergency escape routes satisfying the requirements in case of cabin pressure loss are equally suitable in the event of an engine failure, but conversely a flight route that is suitable for an engine failure scenario must meet the required time conditions determined by the emergency oxygen system aboard in order to qualify. This reduces the number of potential emergency escape routes considerably. As a consequence, high-altitude areas like the Central Asian mountain regions or the Andes are only open to limited passenger air traffic. FIG. 7 shows how an aircraft appropriately certified with respect to its oxygen supply system for a descent within 12 minutes can descend over the Bolivian Andes in an emergency situation. The requirements according to the 12-minute profile make it impossible for the aircraft to land in La Paz, as it cannot maintain the intermediate altitudes and intermediate times according to this profile. This is illustrated by the dashed line 23 representing the descent profile passing east of the city of La Paz, showing that the line 23 passes below the minimum required ground clearance altitude 21, and even below the geographical profile 22 of the terrain. Thus, a descent is possible only in the westward direction, provided the aircraft adopts a position as indicated on the corresponding descent line, or further to the west. For this reason, it is not possible for aircraft with certification for an emergency descent in 12 minutes to fly a route over La Paz, as shown in FIG. 7 by the aircraft positioned to the west. By contrast, in order to be able to overfly this region, an aircraft must be equipped with a high-capacity gaseous emergency oxygen system, so it can descend in 22 minutes in case of a cabin pressure loss, in accordance with its certification. Even then, the intermediate altitudes and intermediate times must be observed. In FIG. 8 a critical point 24 is marked, in which the requirements for an emergency landing in La Paz can no longer be met. If an aircraft with certification according to a 22-minute profile is at an altitude of or even below the critical point 24, it can only follow an emergency escape route leading westward, since otherwise the route is blocked by mountain massif east of La Paz and the descent profile 23 runs beneath the minimum required ground clearance and even below the geographical altitude profile 22 for the terrain. In summary, it may be observed that many limitations are imposed on air traffic due to the problem of cabin depressurization.

In fact, the conventional cabin pressure loss scenario assumes fully functioning engines, which in principle allows airspeeds higher than in the event of engine failure. One might therefore expect that obstacles such as high-altitude terrain could more likely be overflown within the prescribed time interval, thus imposing less stringent requirements on route planning. In reality, however, it must be assumed that cabin depressurization is caused initially by a structural failure, so that the airspeed must be adjusted immediately, that is to say reduced. Therefore, it is not possible to overfly the large expanses of high-altitude terrain without restrictions and still comply with descent profiles described above.

Oxygen undersupply to body tissue in healthy people is usually attributable to an $O_2$-poor environment. Probably, the greatest risk of acute oxygen deficiency for an average healthy human is cabin depressurization in an aircraft. If cabin pressure drops unexpectedly at high flight altitudes, the low partial pressure of oxygen leads to an undersupply of oxygen to body tissue (hypoxia). Hypoxia can result in severe organ damage, possibly even leading to death. One insidious characteristic of hypoxia is that it is not always detected or is detected too late by the person concerned, so he/she is already limited in his/her ability to take corrective action. Symptoms of hypoxia include the spectrum from wrong self-assessment, euphoria, fatigue, disorientation, to unconsciousness. In aviation, hypoxia is considered an extremely serious physical condition, which can have fatal consequences, especially for the crew of an aircraft.

While supplying pure oxygen to humans, the partial pressure of oxygen is increased five-fold. According to Henry's Law, the partial pressure of a gas over a liquid is proportional to the concentration of the gas (physically) dissolved in this liquid. Thus, when supplying the body with pure oxygen, the proportion of the dissolved oxygen in the blood increases five-fold. On the other hand, the gas law does not apply to the oxygen which is chemically bonded to the haemoglobin of red blood cells. Under normal breathing conditions, the oxygen saturation of blood already amounts to 95-100%. Thus, during ventilation mainly the proportion of the physically dissolved oxygen is enriched. The latter is then pressure-dependent. If a human inhales pure oxygen at an atmospheric pressure of 2.5 bar, 20 times the amount of oxygen is dissolved in blood compared to standard conditions. This "systematic hyperbaric oxygenation therapy" is used when low blood oxygen in the body tissue prevents the healing process of patients, or when oxygen must be supplied as a life-saving measure in emergency situations. However, hyperbaric oxygenation has so far not found wide clinical application, mainly because of the side effects of high oxygen content and excess pressure. The oxygen therapy in intensive-care medicine is one of the main causes of oxygen toxicity damage.

The pressure of breathing air is a highly regulating parameter. It can also exert a moderating influence when enriching blood with oxygen. In the case of continuous, controlled ventilation, as in space travel for example, ventilation using pure oxygen must be operated at low pressures, i.e. ambient pressure is not allowed to exceed 0.3 bar. Thus, the barometric pressure and consequently the oxygen partial pressure of the supplied respiratory air is reduced (cf. oxygen partial pressure of 0.21 bar under normal pressure). With continuous ventilation with pure oxygen, the risk of oxygen intoxication is present as early as pressures above said value of 0.3 bar.

Ventilation with pure oxygen can be made possible for various scenarios if the ambient pressure is varied accordingly, but its conflicting characteristics mean that the oxygen cannot be supplied alone in the doses required to counteract oxygen insufficiency without side effects. Surprisingly, it was discovered in experiments and test runs that inhalation of a gas mixture comprising 7±5% $CO_2$ at 15'000 ft altitude, and increasing to 17±5% $CO_2$ at 30'000 ft altitude, vastly improves both the physical and mental functionality of the body in a condition of acute oxygen undersupply, compared to that resulting from pure oxygen supply. The improvement is unprecedented.

If an undersupply of oxygen occurs in the body, the body reacts by accelerating the breathing rate. The increase in the breathing rate causes more oxygen to be inhaled per unit time, but at the same time more carbon dioxide is exhaled. In the body, carbon dioxide is chemically bound as carbonic acid ($H_2CO_3$). From the formula below $$CO_2 + 2H_2O \rightleftharpoons HCO_3^- + H_3O^+ \rightleftharpoons H_2CO_3 + H_2O$$

the chemical balance indicates that reducing $CO_2$ in the body results in the number of $H_3O^+$-ions in the blood to be reduced equally. This causes a shift in the acid-base equilibrium, because the blood becomes increasingly alkaline. In extreme cases, this results in a respiratory alkalosis with symptoms of muscle cramps, impairment of consciousness, even loss of consciousness. Moreover, the increase in the pH-value of blood effects a decrease in the concentration of freely dissolved ionized calcium (hypocalcaemia), leading to hyperexcitability of the musculature and nervous system, exhibiting spasmodic symptoms. Conversely, an increased concentration of carbon dioxide in the blood shifts the pH-value of the blood into the acidic range. Carbon dioxide-sensitive receptors are located on the vessels of many organs. Depending on the specific organ, the blood vessels either contract or expand under the influence of carbon dioxide. The vessels of the brain expand upon an increase of carbon dioxide concentration. The blood-flow rate increases and with it, the oxygen amount reaching the cells per unit time. In this way, the body attempts to compensate for the oxygen undersupply, and in particular, to supply the brain with sufficient oxygen for as long as possible. The opposite effect is observed, if the body is supplied with high oxygen dosage, while reducing the carbon dioxide supply. A hypocapnia, i.e. a low carbon dioxide partial pressure in the arterial blood, leads to contraction of blood vessels in the brain and consequently reduces of the blood and oxygen supply. When cabin pressure is lost in an aircraft, an undersupply of oxygen to the body occurs. The body begins to hyperventilate. Even if a passenger reaches quickly for the artificial respiration mask, the tendency to hyperventilate is further increased by the stress-induced circumstances. Hyperventilation accelerates the rate at which carbon dioxide is exhaled. This reduces the level of carbon dioxide in the body. Since the ventilated air passenger's mobility is limited due to the circumstances, less carbon dioxide is produced by the muscular cells and the effect of the carbon dioxide deficiency is accelerated accordingly. For air passengers, who are restricted to their seats for most of the time, and most particularly in emergency situations, this limitation of mobility may have severe consequences, because the body then produces less carbon dioxide. Not least because of this fact, a rapid descent to a safe flight altitude is essential for survival.

If a dosed, pressure-dependent amount of carbon dioxide is added to the breathing gas, the effects as mentioned in the section above can be diminished. As the active supply of carbon dioxide to the body relaxes blood vessels in the brain, the oxygen supply to the body tissue takes place in a more efficient manner, while at the same time the amount of oxygen is reduced. Oxygen is then reabsorbed more quickly and to a greater extent, and so provided to the tissue and cells, respectively. The gas mixture according to the invention ensures respiration in emergency situations and in doing so, increases the bioavailability of oxygen, in particular oral bioavailability, because carbon dioxide in precisely measured doses acts as a bioenhancer. Finally, because of the gas mixture according to the invention the body is kept at a physiological level of carbon dioxide with just a partial dose of oxygen and over a substantially longer period. This provides significant advantages, particularly in cases of depressurization of aircraft cabins.

Surprisingly, aeromedical experiments have demonstrated that by inhalation of air enriched with carbon dioxide aviation standard values can be attained: for a bridging time of maximally one minute, 84% oxygen saturation of the blood is prescribed, and for bridging time lasting more than one minute, 90% oxygen saturation of the blood is required. For the experiments, test persons were administered the amount of carbon dioxide required to maintain the carbon dioxide level in the blood at a partial pressure of 40 mmHg at different density altitudes. The respiratory air was prepared such that it comprised the following amounts of carbon dioxide at distinct density altitudes: 8% $CO_2$ at 15,000 ft, 11% $CO_2$ at 20,000 ft, and 16.5% $CO_2$ at 30,000 ft. The addition of carbon dioxide to the gas mixture was at the expense of nitrogen. Consequently, the gas mixture for ventilation was composed as follows:
At 15,000 ft density altitude: 21% $O_2$, 8% $CO_2$, 71% $N_2$
At 30,000 ft density altitude: 21% $O_2$, 16.5% $CO_2$, 62.5% $N_2$ Each test person had to undergo two simulated emergency descent profiles from 37,000 ft to 10,000 ft altitude, the descent corresponding to the profiles specified by the ICAO. During the one descent, the test persons inhaled pure oxygen as is usually the case in a cabin pressure loss scenario, and during the other descent, the same test persons inhaled a gas mixture with carbon dioxide added as described above. The experiment was structured in a randomized, double-blind protocol. Neither observers nor test persons knew which gas mixture would be supplied in which descent. The results indicate the following key benefits:
 1. The amount of cabin oxygen aboard an aircraft can be reduced.
 2. Based on the adapted drift-down procedures, more direct flight routes can be flown, thus saving essential costs and time.
 3. Since—as a consequence of the above—less onboard fuel is needed, the cargo capacity of the aircraft increases.
 4. Owing to the reduced fuel consumption the environment is protected.

A particularly elegant aspect of the overall approach regarding the method of additive dosing of carbon dioxide according to the invention is that a passenger himself produces at least part of the required carbon dioxide and oxygen for the purpose of ventilation, respectively. Breathing air under normal ambient pressure consists of approx. 78% nitrogen ($N_2$), 21% oxygen ($O_2$) and approx. 1% residual gases. By contrast, exhaled air consists of approx. 78% nitrogen ($N_2$), 16% oxygen ($O_2$), 4% carbon dioxide ($CO_2$) and approx. 2% residual gases. The exhaled amount of carbon dioxide and oxygen can be recovered. Dosing of the gas mixture according to the invention can thus be accomplished using carbon dioxide and oxygen supplied by the ventilated person him/herself, which is then eventually inhaled again by him/her, while the remaining gas fraction is added synthetically. The higher the density altitude, the more carbon dioxide needs to be dosed additively at the expense of nitrogen.

LIST OF REFERENCE NUMERALS

1 Actual flight route
2 Direct route which may not be flown
3 Minimum required ground clearance
4 Terrain elevation profile
5 Drift-down
6 Gross flight path
7 Net flight path
8 Positive climb gradient begins
9 Route which may not be flown
10 Critical point 1
11 Ideal turn point 1
12 Critical point 2
13 Ideal turn point 2
14 Critical point 3
15 High mountain region
16 Lowland
17 South American west coast
18 Engine failure
19 Optional 22-Minute System
20 Standard 12-Minute System
21 Minimum required vertical clearance
22 Terrain elevation profile
23 Course of the descent profile curve below the terrain elevation profile 22
24 Critical point
Checklist Points (FIG. 5)
 1. Adjust maximum continuous thrust (MCT)
 2. Maintain altitude, decelerate to drift-down speed
 3. Maintain drift-down speed
 4. Select one of the three drift-down options:
   A: Maintain airspeed and climb until fuel burns off
   B: Maintain level flight and accelerate to EOLRC speed gradually (EOLRC=engine-out long-range cruise speed)
   C: Descend and accelerate to EOLRC speed immediately (EOLRC=engine-out long-range cruise speed)

The invention claimed is:
1. A method of ventilating an air passenger in an aircraft, comprising providing a flow of a gas mixture through a ventilation mask, wherein the gas mixture is enriched with $CO_2$ relative to air at sea level, and wherein the amount of enriched $CO_2$ varies from 7±5% CO2 at 15,000 ft flight altitude to 17±5% CO2 at 30,000 ft flight altitude.

2. The method according to claim 1, wherein the enriched gas mixture is obtained in part using carbon dioxide and oxygen supplied by the air passenger.

3. The method according to claim 1, wherein the gas mixture is also enriched with $O_2$ relative to air at sea level.

4. A method of ventilating an air passenger in an aircraft, comprising providing a flow of a gas mixture to act as a bioenhancer and improve the bioavailability of oxygen in the body, wherein the gas mixture is enriched with $CO_2$ relative to air at sea level, and wherein the amount of enriched $CO_2$ comprises 7±5% $CO_2$ at 15,000 ft flying altitude, increasing to 17±5% $CO_2$ at 30,000 ft flying altitude.

5. The method according to claim 4, wherein the gas mixture is delivered to the air passenger through a respiration mask.

6. The method according to claim 4, comprising adding carbon dioxide to pure $O_2$ or to a mixture comprising a fraction of $N_2$ and a fraction of $O_2$ for ventilation.

\* \* \* \* \*